(12) United States Patent
Xie et al.

(10) Patent No.: US 11,833,180 B2
(45) Date of Patent: Dec. 5, 2023

(54) MEDICAL APPLICATIONS OF CANNABIS AND HEMP EXTRACTS

(71) Applicant: Shuang Xie, Richmond (CA)

(72) Inventors: Shuang Xie, Richmond (CA); Betty Cai, Stanford, CA (US); Allen Xie, Richmond (CA)

(73) Assignee: Shuang Xie, Richmond (CA)

( * ) Notice: Subject to any disclaimer, the term of this patent is extended or adjusted under 35 U.S.C. 154(b) by 116 days.

(21) Appl. No.: 17/449,794

(22) Filed: Oct. 1, 2021

(65) Prior Publication Data

US 2022/0105146 A1 Apr. 7, 2022

Related U.S. Application Data

(60) Provisional application No. 63/086,076, filed on Oct. 1, 2020, provisional application No. 63/086,072, filed on Oct. 1, 2020.

(51) Int. Cl.
*A61K 36/185* (2006.01)
*A61K 9/02* (2006.01)
*A61K 9/70* (2006.01)

(52) U.S. Cl.
CPC .............. *A61K 36/185* (2013.01); *A61K 9/02* (2013.01); *A61K 9/7084* (2013.01); *A61K 2236/30* (2013.01); *A61K 2236/51* (2013.01)

(58) Field of Classification Search
None
See application file for complete search history.

(56) References Cited

FOREIGN PATENT DOCUMENTS

CA 3025080 A1 * 1/2018

* cited by examiner

*Primary Examiner* — Michael V Meller
(74) *Attorney, Agent, or Firm* — SYNCODA LLC; Feng Ma

(57) ABSTRACT

A method of preparing medical composition including hemp or *Cannabis* full plant extracts, cannabinoids, and one or more pharmaceutically acceptable excipients containing active pharmaceutical ingredients (APIs) can produce suppositories, patches, cream, lipstick or other skin care cosmetic. *Cannabis*, hemp plant chemicals and APIs can be delivered to one's bloodstream. The suppository composition is formulated for effective absorption through the mucosal membrane. The suppository is useful for the administration of medicine to treat pain, nausea, post-operative ileus, and/or inflammatory bowel diseases in patients with nausea, vomiting, other conditions preventing swallowing, or conditions wherein suppository administration is required.

1 Claim, 4 Drawing Sheets

Δ⁹-tetrahydrocannabinol (Δ⁹-THC)　　　Cannabidiol (CBD)

Δ⁸-tetrahydrocannabinol (Δ⁸-THC)

Δ⁹-tetrahydrocannabinolic acid (Δ⁹-THCA)　　　Cannabidiolic acid (CBDA)

MEDICAL APPLICATIONS OF CANNABIS AND HEMP EXTRACTS

CROSS-REFERENCE TO RELATED APPLICATIONS

This application claims priorities under 35 U.S.C. 119(e) to U. S. Provisional Patent Application Ser. Nos. 63/086,076 and 63/086,072, both filed on Oct. 1, 2020, the disclosures of which are hereby incorporated by reference in their entirety.

BACKGROUND

*Cannabis* has been a medicinal plant for millennia. Recent developments in medical science have propelled growing interest in the medicinal effects and uses of *Cannabis* and hemp, which produces a group of natural substances include cannabinoids, terpene, wax, lipids, etc. by extraction from biomass. Clinical studies are discovering an increasing number of unique properties and therapeutic benefits present in the substances. The medicinal uses of *Cannabis* include (1) treatment of nausea and pain associated with cancer and chemotherapy; (2) nausea, pain and wasting associated with AIDS; (3) arthritis and rheumatism; (4) glaucoma; (5) migraines; (6) muscle spasticity associated with multiple sclerosis and paralysis; (7) alcohol and narcotics withdrawal; (8) stress and depression; (9) asthma; and (10) epileptic seizures. *Cannabis* extracts have displayed herbal synergy encompassing potentiation by active or inactive components, antagonism, summation, and pharmacokinetic and metabolic interactions.

SUMMARY

This disclosure relates to methods of hemp and *Cannabis* extraction which enable the use of *Cannabis* extracts for medical applications. Separation of cannabinoids from full plant crude extracts has been found to produce a variety of byproducts, including terpenes, wax, plant sterols, fatty acids, flavonoids, and essential vitamins and nutrients. Cannabinoids with controlled profile and dosage can be added back to the byproduct and applied in patch or cream form for immediate pain relief A pharmaceutical topical composition comprising the full plant extract, including wax and terpene, derived as byproducts during extraction and purification of cannabinoids is disclosed. Embodiments of the disclosure also relate to suppositories with analgesic or anti-inflammatory effects. Since active pharmaceutical ingredients (APIs) are administered away from gastrointestinal tracts, application of the suppository is not accompanied by side effects such as peptic ulcer, bleeding in constipation, and diarrhea. As a result, it is particularly suitable for patients with disorders in the digestive organs and infant patients. APIs are released constantly over a extended period of time.

Various embodiments of this disclosure provide a novel method to produce extracts from the *Cannabis* plant and separate the extracts to be formulated for various medical applications. To achieve more potent results and enable the large-scale production of *Cannabis* extracts, two primary methods for efficient extraction are used: Carbon dioxide ($CO_2$) extraction and solvent extraction. The resultant crude extracts include cannabinoids, terpenes, wax, plant sterols, fatty acids, flavonoids, and essential vitamins and nutrients. Terpenes are the naturally occurring compounds that infuse *Cannabis* with its signature aromas and flavors as well as some of its potential therapeutic benefits. Crude extracts are less suitable for use in pharmaceutical formulations, and purified forms of certain cannabinoids are preferred in most applications. Fractional distillation, immiscible liquid-liquid separation, or preparative and flash chromatography have been employed either individually or in combination to separate desirable components of plant extracts from their less-desirable counterparts in other pharmaceutical plant preparations and natural products such as essential oils. However, these techniques either tend to be difficult to scale up and make continuous or tend to degrade the molecules of interest. Winterization is the process of removing fats and waxes from the hemp extract in an apparatus illustrated in FIG. 4. The process involves dissolving the CBD oil coming out of the $CO_2$ extractor in food-grade ethanol and subsequently chilling the ethanol oil mixture down to $-20°$ C. The fats and waxes are less soluble at these temperatures and will precipitate while the cannabinoids remain in solution. The fats and waxes are then filtered out as byproducts before solvent removal. Although more and more large-scale *Cannabis* extraction has been in production, the byproducts have not been used in the industry and created a huge waste.

Embodiments of the present disclosure address the needs described above and relate to the formulation of patches or suppositories using winterization byproducts as the base for medical applications of APIs.

Another objective of the present disclosure is to provide processes which fully utilize all products from *Cannabis* or hemp extraction, including byproducts, without degradation of the compounds. The carbon dioxide ($CO_2$) and solvent extraction methods, as well as the winterization process, employ low-temperature processes to prevent degradation and retain the bioactivity of compounds.

Another objective of the present disclosure is to provide a composition that serves as an easy and accurate means to control dosage amounts of cannabinoid concentrates and extracts for the treatment of medical conditions and symptoms. A standardized and measurable dosage of cannabinoids with or without $\Delta^8$-THC, enabling patients to accurately and repeatably deliver the same dose to address their medical needs, is proposed.

Another objective and advantage of the present disclosure is to provide a few convenient ways to consume and make use of the full plant extracts according to the basic mechanisms of synergy proposed (Wagner and Ulrich-Merzenich, *Phytomed.* 2009; 16:97-110): (i) multi-target effects; (ii) pharmacokinetic effects such as improved solubility or bioavailability; and (iii) agent interactions.

Another embodiment of the disclosure is a rectal suppository comprising byproducts with $\Delta^8$-THC or other cannabinoids and one or more pharmaceutically acceptable excipients, wherein the total weight of the suppository ranges from about 500 mg to about 3000 mg.

In another aspect, a rectal suppository containing *Cannabis* and hemp extracts is provided, wherein the suppository comprises from about 20 mg to about 500 mg of cannabinoids with $\Delta^8$-THC distillate and the wax and fat byproduct base has an ascending melting point between 31 and 36° C.

In some embodiments, the base can be selected from either one or a mixture of the following ingredients: hemp or *Cannabis* extraction byproducts, coconut oil, cocoa butter, yellow beeswax, etc.

In some embodiments, the method further comprises heating of the base mixed with cannabinoids or other active ingredients to reduce its viscosity and reach homogeneity.

In some embodiments, the mixture is heated to between 37 and 60° C.

In some embodiments, the method further comprises: testing the mixture to determine the cannabinoid and terpene profile and determining percentage by weight; determining the amount of a desired individual dose of APIs; determining the number of desired individual doses of cannabinoids; and determining the total number of desired individual doses.

DETAILED DESCRIPTION

Unless defined otherwise, all technical and scientific terms used herein have the same meaning as commonly understood by one of ordinary skill in the art to which the disclosure belongs. Although any methods and materials similar or equivalent to those described herein can be used in the practice or testing of the present disclosure, the preferred methods and materials are described. All publications mentioned hereunder are incorporated herein by reference.

There is a growing base of evidence on the various medicinal benefits of *Cannabis*, including its efficacy in the treatment of conditions such as migraines, cramps, and convulsions. A 2017 report issued by the National Academy of Sciences, Engineering, and Medicine indicated conclusive or substantial evidence that *Cannabis* or cannabinoids are effective for relieving chronic pain in adults, treating chemotherapy-induced nausea and vomiting, and improving patient-reported multiple sclerosis spasticity symptoms. Moreover, the report indicated evidence that *Cannabis* or cannabinoids are effective for improving sleep outcomes for patients with obstructive sleep apnea syndrome, fibromyalgia, chronic pain, and multiple sclerosis.

Figure 1:
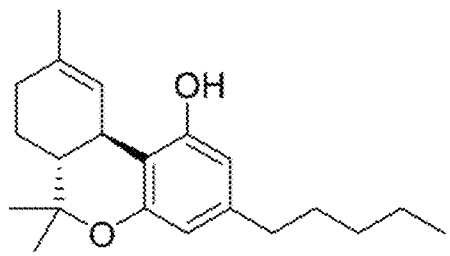
FIG. 1 illustrates chemical structures of cannabinoid compounds.
Figure 1:
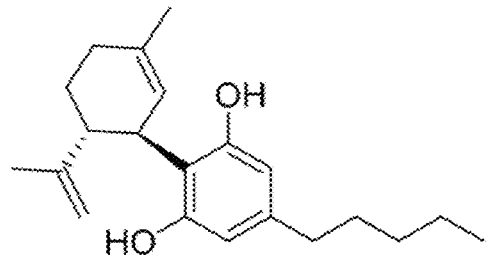
Figure 1:
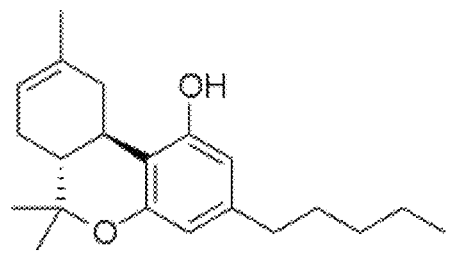
Figure 1:
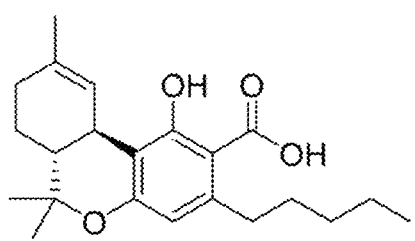
Figure 1:
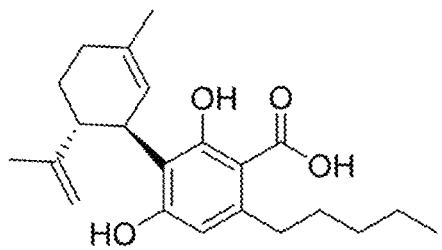

The *Cannabis* plant contains many naturally occurring substances that are of great interest in science and medicine. There are a total of eighty-five (85) cannabinoids isolated from the *Cannabis* plant. Isolated compounds from the *Cannabis* plant include, among others, $\Delta^9$-tetrahydrocannabinolic acid ($\Delta^9$-THCA), cannabidiolic acid (CBDA), $\Delta^9$-tetrahydrocannabinol (THC), cannabidiol (CBD), (shown in FIG. 1), cannabichromene (CBC), cannabigerol (CBG), and cannabidivarin (CBDV). While THC has psychoactive effects, other compounds such as CBD, CBC, CBG, and CBDV do not. The principal cannabinoids present in herbal *Cannabis* are the cannabinoid acids $\Delta^9$-tetrahydrocannabinolic acid ($\Delta^9$-THCA) and cannabidiolic acid (CBDA) with small amounts of the respective neutral (decarboxylated) cannabinoids. Cannabidiol (CBD) is the decarboxylated product of cannabidiolic acid (CBDA) and results from the heating of CBDA to about 130° C.

Medical *Cannabis* has been legally available for patients in many countries. Licensed producers produce a variety of *Cannabis* strains with different concentrations of cannabinoids. Cannabinoids in most medical *Cannabis* are decarboxylated when subjected to heating for consumption by patients or when extracted for preparing *Cannabis* derivative products. Even though *Cannabis* extracts have been used for thousands of years, there is little understanding of the true chemical composition of *Cannabis* extracts, changes occurring during heating of the extracts, and their relevance to pharmacological effects. The extract from a popular commercial strain of medical *Cannabis* prior to and after decarboxylation was investigated to understand the chemical profiles (Lewis et al, *ACS Omega.* 2017 Sep. 30; 2(9): 6091-6103). A total of up to 62 compounds were identified simultaneously in the extract derived from commercial *Cannabis*, including cannabinoids, terpenes, fatty acids, and other common phytochemicals. As medical *Cannabis* gains more acceptance in society and healthcare practitioners become more acquainted with the therapeutic benefits of this plant product, the need for standardization and consistency of the chemical constituents beyond THC and CBD in the medical *Cannabis* strains is immediate. Yang et al. discloses a method to predict the relationship between the chemical composition, including cannabinoids, of *Cannabis* extracts and cannabinoid receptor responses (Yang et al. in *Molecules.* 2020 August; 25(15): 3466). Furthermore, basic and clinical sciences supporting proper dosage forms yielding adequate pharmacological activity and outlining the potential adverse effects and risks of *Cannabis* consumption are also urgently needed; however, these are immensely dependent on the chemical constituents of the extracts consumed by patients. Given the inconsistency and misrepresentation of *Cannabis* in the marketplace, new metered dosing modalities would help facilitate the adoption of medical *Cannabis* extract-based products by the wider medical community.

More recently, the synergistic contributions of cannabidiol to *Cannabis* pharmacology and analgesia have been scientifically demonstrated. Other cannabinoids, including tetrahydrocannabivarin, cannabigerol, and cannabichromene, exert additional effects of therapeutic interest (Russo et al., *Br J Pharmacol.* 2011 August; 163(7):1344-64). Another echelon of phytotherapeutic agents, the *Cannabis* terpenoids such as limonene, myrcene, α-pinene, linalool, β-caryophyllene, caryophyllene oxide, nerolidol and phytol, share a precursor with phytocannabinoids and are flavor and fragrance components common to human diets that have been designated "Generally Recognized as Safe" by the U.S. Food and Drug Administration and other regulatory agencies. Terpenoids are quite potent and affect animal and even human behavior when inhaled from ambient air at serum levels in the single-digit ng·mL$^{-1}$. They display unique therapeutic effects that may contribute meaningfully to the entourage effects of *Cannabis*-based medicinal extracts. Focus will be placed on phytocannabinoid-terpenoid interactions that could produce synergy with respect to treatment of pain, inflammation, depression, anxiety, addiction, epilepsy, cancer, and fungal and bacterial infections (including methicillin-resistant *Staphylococcus aureus*). Scientific evidence is presented for non-cannabinoid plant components as putative antidotes to the intoxicating effects of THC that could increase its therapeutic index. Synergistic effects can be produced if the constituents of an extract affect different targets or interact with one another to improve the solubility and thereby enhance the bioavailability of one or several substances in an extract. Phytocannabinoid-terpenoid synergy increases the likelihood that an extensive pipeline of new therapeutic products is possible from the *Cannabis* plant.

Cannabinoids are a family of compounds that interact with cannabinoid receptors in the human body. Many research studies have confirmed the medicinal value of cannabinoids. For instance, cannabinoids have been investigated for possible treatment of seizures, nausea, vomiting, lack of appetite, pain, arthritis, inflammation, and other conditions. $\Delta^9$-tetrahydrocannabinol ($\Delta^9$-THC) is the psychoactive ingredient commonly found in marijuana. $\Delta^9$-THC is one of around 60 cannabinoids present in the *Cannabis sativa* plant. It is the most well-known cannabinoid and is responsible for the characteristic psychoactive effect of *Cannabis*. In contrast, $\Delta^8$-THC is an isomer of $\Delta^9$-THC that is less abundant in the *Cannabis* plant and has been studied less extensively in prior research. $\Delta^8$-THC is one of around 60 cannabinoids that naturally occur in the *Cannabis* plant. $\Delta^8$-THC is found in very low concentrations (<0.1%) in CBD hemp flower. It can also be extracted or converted from other cannabinoids and produced in concentrated form for a variety of uses. As compared to $\Delta^9$-THC, $\Delta^8$-THC produces less intense psychometric effects and holds potential to be used in a variety of medical treatments. For instance, research has indicated that $\Delta^8$-THC is 100% more effective than $\Delta^9$-THC in reducing chemotherapy-induced nausea in pediatric cancer patients. Furthermore, the use of $\Delta^8$-THC as an anti-emetic was found to completely prevent vomiting while producing negligible side effects (Abrahamov et al, 1995, *Life Sci.* 56:2097-2102). In addition, various studies have suggested that $\Delta^8$-THC is an effective therapeutic agent for a range of medical conditions, for instance in reducing pain and inflammation associated with corneal injury and stimulating appetite following weight loss (Avraham et al, 2004, *Pharmacol. Biochem. Behav.* 77:675-684; Thapa et al, 2018, *Cannabis* Cannabinoid Res. 3.1:11-20). Consequently, therapies involving $\Delta^8$-THC and $\Delta^9$-THC hold potential to address a variety of medical conditions and are the subject of further study and implementation.

The IUPAC nomenclature of $\Delta^9$-THC or THC is (−)-(6aR, 10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. These are among the most prominent compounds in the family of compounds extracted from the *Cannabis* plant referred to as cannabinoids.

The crude oil that is made with methods such as supercritical $CO_2$ extraction or hydrocarbon extraction contains terpene, waxes, and lipids in addition to cannabinoids which can be harsh or have undesirable tastes when smoked or vaporized. Remaining waxes and lipids can dilute product potency and result in a lesser-quality distillate. Consequently, it is very important to properly winterize and filter those remaining waxes and lipids to create desirable *Cannabis* products. These waxes and lipids are winterization byproducts from crude extract. Although byproducts from the isolation of cannabinoids are found to be useful in general, the byproducts are not applicable in most edible or topical products due to the undesirable smell and color. However, the byproducts containing wax have the characteristics required for use in patches and suppositories, alternative routes of administration which avoid or minimize the side effects. Suppositories have been demonstrated to have the ability to deliver analgesics to local tissue as well as systemically deliver pain relief They are often used as an alternative to oral administration to deliver drugs to patients that have difficulty swallowing or adhering to pills. Additionally, suppositories have pharmacokinetic advantages by increasing bioavailability to absorbable tissue, bypassing first-pass metabolism, and enabling the delivery of high doses of drug and avoiding irritation to the gastric mucosa. Suppositories also represent a dosage form that is suitable for both vaginal and rectal administration without additional applicators, equipment, or special storage conditions. The adaptable cannabinoids in suppository formulations allow for a greater number of drugs to be incorporated in formulations.

Cannabinoids can be isolated from crude extraction directly from plants in the *Cannabis* genus, including *Cannabis sativa*, *Cannabis ruderalis*, and *Cannabis indicia*. In patent US20190008823A1, Changoer et al. describes a method to combine separated and encapsulated cannabinoids with conventional bases. However, the separation of the crude extracts resulted in a large amount of byproduct composing of many compounds, including plant wax and lipids which have an unpleasant smell and taste. Taking into account their limitations and potential therapeutic benefits, the effective medical application of these byproducts is disclosed.

$\Delta^8$-THC has the IUPAC nomenclature of (−)-(6aR,10aR)-6,6,9-trimethyl-3-pentyl-6a,7,8,10a-tetrahydro-6H-benzo[c]chromen-1-ol. It is rarely extracted directly from plants but can instead be obtained by conversion from THC and/or CBD. $\Delta^8$-THC is a double-bond isomer of THC and a minor constituent of most varieties of *Cannabis* (Hollister and Gillespie, 1972, *Clin Pharmacol Ther* 14: 353). The main chemical difference between the two compounds is that THC is easily oxidized to cannabinol, whereas $\Delta^8$-THC is not and is in fact very stable. $\Delta^8$-THC, for the most part, produces similar psychometric effects as does $\Delta^9$-THC, but is generally considered to be 50% less potent than $\Delta^9$-THC and has been shown in some cases to be 3-10 times less potent. $\Delta^8$-THC has also been shown to be more (200%) effective as an anti-emetic than $\Delta^9$-THC and has been used as an anti-emetic in children, based on the belief that the side effects of $\Delta^9$-THC and $\Delta^8$-THC, such as anxiety and dysphoria, are more prevalent in adults than children (Abrahamov et al, 1995, *Life Sciences* 56: 20972102). It is also of note that the effect of mixed Cannabinoids (THC and CBD) on $\Delta^8$-THC has not been investigated.

In patients suffering from Acquired Immune Deficiency Syndrome (AIDS), lack of appetite, nausea, vomiting, and pain are common related symptoms. A variety of cannabinoids, including $\Delta^8$-THC, are used to treat these conditions. Similarly, symptoms associated with Parkinson's disease such as tremors are also treated with cannabinoids. In addition, various other conditions may be treated or alleviated by the absorption of cannabinoids and derivatives thereof. Conditions that may be treated or alleviated include nausea, vomiting, emesis, pain, lethargy, alcohol induced disorders, multiple sclerosis, inflammatory bowel disorders, arthritis, dermatitis, systemic lupus erythematosus, inflammation, convulsions, psychotic episodes, some cancers, peripheral neuropathic pain, diabetic neuropathy, shingles, burns, actinic keratosis, oral cavity sores and ulcers, seborrheic dermatitis, ankylosing spondylitis, Reiter syndrome, psoriatic arthritis, joint pain, chondrocalcinosis, fibromyalgia, musculoskeletal pain, polymyositis, neuropathic-postoperative complications, acute nonspecific tenosynovitis, epicondylitis, bursitis, post-traumatic osteoarthritis, juvenile rheumatoid arthritis, synovitis, pancreatitis, contact dermatitis, bullous dermatitis herpetiformis, eczema, mycosis fungoides, pemphigus, severe erythema multiforme, seborrheic dermatitis, and seizures. Cannabinoids are further shown to have broad antioxidant and neuroprotective properties along with immunomodulatory effects. Clinical studies have identified a variety of unique properties and therapeutic benefits in $\Delta^8$-THC. There is a growing base of evidence on the diverse medicinal benefits of $\Delta^8$-THC, from its anti-inflammatory properties and efficacy in alleviating painful conditions such as migraines, cramps, and convulsions to its ability to provide relaxation against diseases such as epilepsy and anxiety.

When used by humans medicinally or recreationally, *Cannabis* can be consumed via a variety of routes, including via vaping or smoking dried flower buds and leaf portions, resins, extracted oils, or waxes. In recent years, many medical patients and recreational users have begun to prefer the consumption of *Cannabis* in edible form, for instance by eating lozenges, candies, or baked goods, drinking beverages, or taking tablets or capsules. Topical applications such as cream, patches, or mucosal drug delivery techniques have been of extensive interest in the research domain. Advantages of this route over other routes of administration include avoiding the first-pass metabolism and minimizing gastric irritation.

The rectum has an abundant blood supply, absence of villi, and a relatively small surface area. In addition, the rectum also contains a small volume of viscous fluid (0.5-1.25 mL) spread over the surface with limited buffer capacity. The rectal route of administration is specifically useful for people who have difficulty swallowing, during nausea and vomiting conditions, and when the patient is unconscious. Suppositories are a dosage form designed to deliver drugs through rectal and vaginal routes of administration. They evolved as a more convenient alternative form of drug delivery from liquid enema formulations. Despite a long history of use for rectal and vaginal drug delivery, the current worldwide market for suppositories is limited primarily due to a lack of rational pharmaceutical development. In spite being a noninvasive route of administration, the human rectum remains to be a relatively unexplored route of drug delivery.

Suppositories in solid dosage form have been prepared using either lipophilic or hydrophilic bases. These suppositories either melt or dissolve in body fluids, thereby releasing the entrapped drug. Suppositories offer several advantages over other dosage forms. Current suppository designs have integrated active pharmaceutical ingredients (APIs) into existing formulation designs. Emerging suppository development has been focused on improving upon the existing classical design to enhance drug delivery and is poised to enable the use of suppository drug delivery with a broader range of drugs. With continuing research into rational suppository design and development, there is significant potential for cannabinoids suppository drug delivery.

Figure 2:
FIG. 2 illustrates schematic diagrams of typical suppository shapes including bullet or torpedo, round oval, elongated oval, tampon, and teardrop or cone.

Suppositories have classically been small round or cone-shaped medications designed to be inserted into the vagina, anus, or urethra. Commonly used shapes for suppositories include round and elongated ovals, tampon, and 'teardrop' or 'cone' (FIG. 2). These suppositories can be composed of, but not limited to, cocoa butter, coconut oil, glycerinated gelatin, hydrogenated vegetable oils and hard fats, polyethylene glycols (PEGs), and fatty acid esters of PEG. With a combination of these excipient bases, suppositories have fallen into one of two major types: lipophilic-based or hydrophilic-based. The lipophilic fat-based suppositories melt at body temperature to release drugs into the body. They readily solubilize typical insoluble small-molecule drugs and require no localized fluids to spread and release the drug. Typically, such suppositories are ideal for the rectum, where little fluid is available in the lower large intestinal tract. The hydrophilic water-based suppositories are unaffected by body temperature and require water to dissolve the suppository and release the drug. Such water-based suppositories are appropriate for vaginal application, where more local fluid is available. These two different types of suppositories have allowed this dosage form to become increasingly specific for drug delivery. Avoiding first-pass metabolism through the liver is possible by keeping the dosage form, and thus the released drug, in the lower part of the rectum. The lipophilic or hydrophilic nature of suppository formulations allow for a greater number of antiviral drugs to be incorporated than current semisolid formulations. A hydrophilic suppository will first dissolve in the fluid or melt on the mucous layer, depending on whether it is hydrophilic or lipophilic. Due to osmotic effects of the dissolving vehicle, water is drawn to the rectum or vagina; as the suppository dissolves or melts and spreads, drugs dissolved in the suppository will diffuse out toward the mucosal epithelial surfaces. When a lipophilic suppository liquifies under heat, the drug transport observed in dissolving suppositories will occur in melting suppositories. Administration of drugs through suppositories is compatible to both topical and systemic routes of drug delivery.

These, and other advantages and features of various embodiments of the present disclosure, are described with specificity to make the present disclosure understandable to one of ordinary skill in the art.

Various products containing hemp extract have been marketed in recent years. For instance, $\Delta^8$-THC is generally produced in distillate form and can be converted from CBD. Most cannabinoids, including $\Delta^8$-THC, may be consumed by digestion or by transdermal delivery, vape or smoking. A more effective method to deliver cannabinoids for rapid absorption by a mammal, preferably a human being, has yet to be developed. The present disclosure offers a method to deliver $\Delta^8$-THC and other *Cannabis* extracts while minimizing the adverse effects induced by other methods of delivery.

As used herein, CBD refers to cannabidiol.

As used herein, $\Delta^8$-THC refers to $\Delta^8$-tetrahydrocannabinol.

As used herein, $\Delta^9$-THC refers to $\Delta^9$-tetrahydrocannabinol.

Described herein is a method of converting cannabidiol (CBD) to a $\Delta^8$-THC containing cannabinoids that comprises the following steps: providing a reaction mixture comprising a catalyst without organic solvent, adding CBD isolate or hemp and *Cannabis* extracts containing CBD, heating and mixing said reaction mixture, and distilling the cannabinoids from the mixture. The cannabinoids having $\Delta^8$-THC may then be combined with suitable excipients to form a pharmaceutical composition.

In some embodiments, $\Delta^8$-THC at therapeutically effective concentrations or dosages may be combined with a pharmaceutically or pharmacologically acceptable carrier, excipient, or diluent, which can be either the extract byproduct or other possible carriers, including but not limited to poly(ethylene-vinyl acetate), copolymers of lactic acid and glycolic acid, poly(lactic acid), gelatin, collagen matrices, polysaccharides, poly(D,L lactide), poly(malic acid), poly (caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl mono stearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, non-crystalline cellulose, magnesium aluminum silicate, triethanolamine, polyvinyl alcohol, and polyvinylpyrrolidone.

Purity is determined by analytical HPLC and GC-MS. In GC-MS, the mass of analyte detected in a sample is proportional to its peak area in the total ion chromatogram. If the masses are generally in the same range, the peak areas of individual compounds may be compared with the total peak area of the GC-MS chromatogram.

The following examples describe common uses of the disclosure; however, the disclosure is by no means limited to the examples listed.

Example 1

Figure 3:
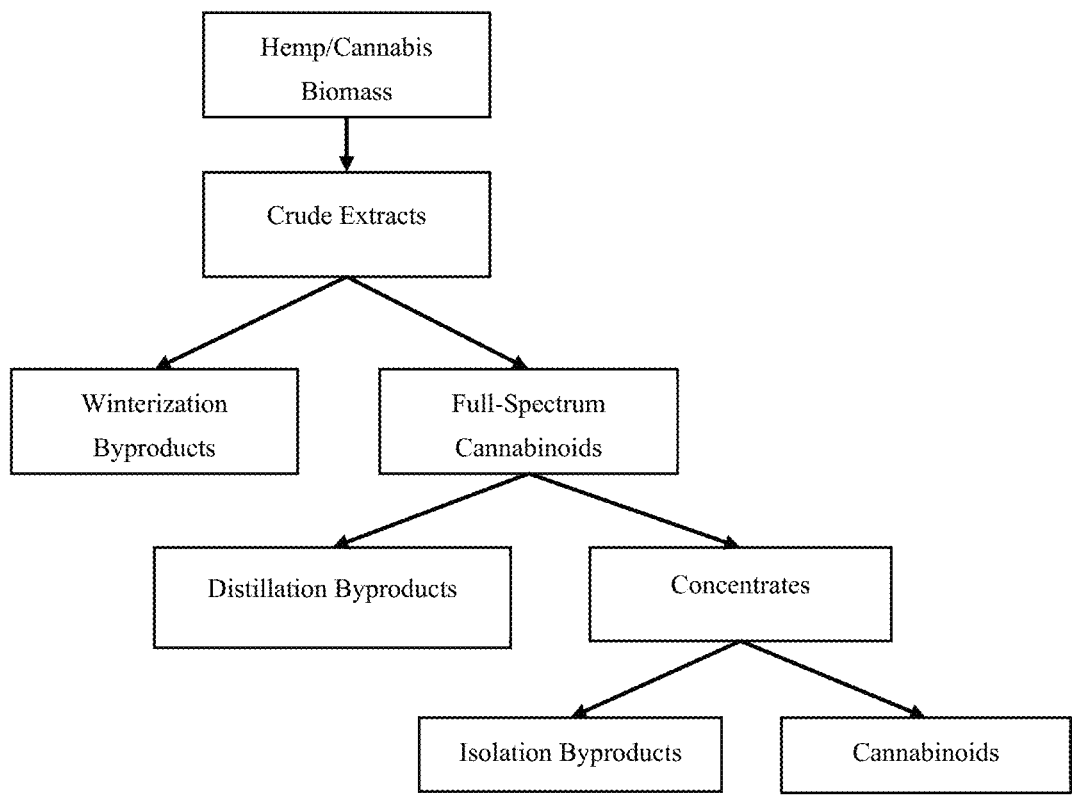
FIG. 3 schematically illustrates processes of *Cannabis* and hemp extraction.
Figure 4:
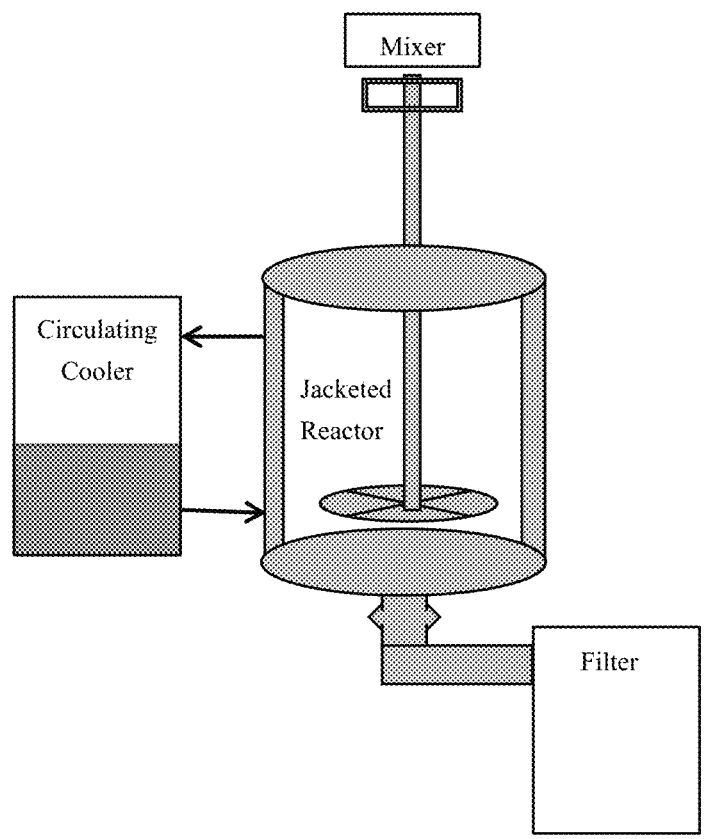
FIG. 4 schematically illustrates a winterization apparatus for *Cannabis* and hemp extraction.

Prepare a 120 L jacketed reactor that contains a mixer and circulating cooler. The reactor is connected to a filter (see FIG. 3).

Add 20 L of $CO_2$ hemp crude extracts consisting of 50% CBDA, 10% CBD, 2% THCA etc. and 60 L of ethanol to the reactor.

Begin stirring and mixing.

After the mixture is homogenously mixed, stop the mixer and start cooling the mixture to a low temperature of −20° C. to allow for winterization.

Filter the mixture at low temperature and collect the solid portion from the filtrate as winterization byproducts. The winterized byproducts were dried under vacuum and weighted about 2 kg consists of mostly hemp wax and were subjected to testing, with the certificate of analysis indicating a composition of 5% CBDA and 1% CBD.

Recover ethanol from the liquid portion of the filtrate and collect the extracts. The extracts could be subjected to further purification methods, including distillation and further isolation. The distillates and isolate may then be converted to $\Delta^8$-THC.

Example 2

A rectal suppository comprising the above winterization byproduct and $\Delta^8$-THC was prepared as follows: About 0.1 kg of $\Delta^8$-THC concentrate was added to a homogenous melt containing about 2 kg of the above winterized byproduct at a temperature of about 50° C. The $\Delta^8$-THC and suppository base were mixed gently until homogenous and subsequently poured into a mold. Upon cooling, the suppository was removed from the mold.

Example 3

Prepare a 120 L jacketed reactor that contains a mixer and a circulation cooler. The reactor is connected to a filter (see FIG. 3).

Add 20 L of $CO_2$ *Cannabis* crude extracts consisting of 50% THCA and 10% THC etc. and 60 L of ethanol to the reactor.

Begin stirring and mixing.

After the mixture is homogenously mixed, stop the mixer and start cooling the mixture to a low temperature of −20° C. to allow for winterization.

Filter the mixture at low temperature and collect the solid portion from the filtrate as winterization byproducts. The winterized byproducts were dried under vacuum and weighted about 2 kg subjected to testing, with the certificate of analysis indicating a composition of 8% THCA and 1% THC.

Recover ethanol from the liquid portion and collect the extracts. The extracts may be subjected to further purification and distillation, with the final resultant distillates consisting of 90% THC.

Example 4

A rectal suppository comprising the winterization byproduct and $\Delta^8$-THC was prepared as follows: About 0.1 kg of $\Delta^8$-THC concentrate was added to a homogenous melt containing about 2 kg of the above winterized byproduct at a temperature of about 45° C. The $\Delta^8$-THC and suppository base were mixed gently until homogenous and subsequently poured into a mold. Upon cooling, the suppository was removed from the mold.

Example 5

A rectal suppository comprising the winterization byproduct was prepared as follows: About 2 kg of the above winterized byproduct was heated at a temperature of about 45° C. and subsequently poured into a mold. Upon cooling, the suppository was removed from the mold.

Example 6

A simple patch comprising the winterization byproduct and $\Delta^8$-THC was prepared as follows: About 0.1 kg of $\Delta^8$-THC concentrate was added to a homogenous melt containing about 2 kg of the above winterized byproduct at a temperature of about 45° C. The components were mixed gently until homogenous, then smeared or wiped on a patch substrate. The surface is covered with a plastic layer before carefully packaging the product.

It will be readily apparent to those skilled in the art that various modifications and changes may be made without departing from the spirit and the scope of the present disclosure. Any ranges, ratios, and range of ratios that can be derived from the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

Although specific embodiments of the disclosure have been disclosed, those having ordinary skill in the art will understand that changes can be made to the specific embodiments without departing from the spirit and scope of the disclosure. The scope of the disclosure is not to be restricted, therefore, to the embodiments disclosed.

What is claimed is:

1. A suppository consisting essentially of a cannabis extract, cocoa butter, coconut oil, polyethylene glycol, polyvinylpyrrolidone, gum acacia, methyl cellulose and gelatin.

\* \* \* \* \*